(12) United States Patent
Ujihara et al.

(10) Patent No.: US 9,284,246 B2
(45) Date of Patent: Mar. 15, 2016

(54) METHOD FOR PRODUCING OPTICALLY ACTIVE 2,3-DIHYDROFARNESAL

(71) Applicant: TAKASAGO INTERNATIONAL CORPORATION, Tokyo (JP)

(72) Inventors: Hideo Ujihara, Yokohama (JP); Mitsuhiko Fujiwhara, Chigasaki (JP)

(73) Assignee: TAKASAGO INTERNATIONAL CORPORATION, Tokyo (JP)

( * ) Notice: Subject to any disclaimer, the term of this patent is extended or adjusted under 35 U.S.C. 154(b) by 0 days.

(21) Appl. No.: 14/425,115

(22) PCT Filed: Sep. 6, 2013

(86) PCT No.: PCT/JP2013/074108
§ 371 (c)(1),
(2) Date: Mar. 2, 2015

(87) PCT Pub. No.: WO2014/038665
PCT Pub. Date: Mar. 13, 2014

(65) Prior Publication Data
US 2015/0218072 A1      Aug. 6, 2015

(30) Foreign Application Priority Data
Sep. 7, 2012 (JP) ............................ 2012-197450

(51) Int. Cl.
*C07C 45/00* (2006.01)
*C07C 211/21* (2006.01)
*C07B 53/00* (2006.01)
*C07C 47/21* (2006.01)

(52) U.S. Cl.
CPC .............. *C07C 45/00* (2013.01); *C07B 53/00* (2013.01); *C07C 47/21* (2013.01); *C07C 211/21* (2013.01)

(58) Field of Classification Search
CPC ............................ C07C 45/516; C07C 209/60
USPC .......................................... 568/450; 564/485
See application file for complete search history.

(56) References Cited

U.S. PATENT DOCUMENTS

| | | | |
|---|---|---|---|
| 4,695,631 A | 9/1987 | Otsuka et al. | |
| 5,753,610 A | 5/1998 | Harada et al. | |
| 5,942,272 A | 8/1999 | Kaiser | |
| 2010/0105958 A1 | 4/2010 | Scheibel et al. | |
| 2010/0137649 A1 | 6/2010 | Scheibel et al. | |
| 2011/0034363 A1 | 2/2011 | Price et al. | |
| 2012/0010423 A1 | 1/2012 | Scheibel et al. | |
| 2012/0010432 A1 | 1/2012 | Scheibel et al. | |

FOREIGN PATENT DOCUMENTS

| | | |
|---|---|---|
| EP | 0 068 506 A1 | 1/1983 |
| EP | 0 731 160 A2 | 9/1996 |
| JP | 56-156240 A | 12/1981 |
| JP | 58-004748 A | 1/1983 |
| JP | 58-177942 A | 10/1983 |
| JP | 58-177943 A | 10/1983 |
| JP | 60-042343 A | 3/1985 |
| JP | 08-003092 A | 1/1996 |
| JP | 08-245979 A | 9/1996 |
| JP | 2012-502922 A | 2/2012 |

OTHER PUBLICATIONS

Dietmar Bartschat et al., "Chiral Compounds of Essential Oils XXI: (E, Z)- 2,3-Dihydrofarnesals-Chirospecific Analysis and Structure Elucidation of the Stereoisomers," Phytochemical Analysis, 1997, pp. 159-166, vol. 8, No. 4.
Anna Luxova et al., "Absolute Configuration of Chiral Terpenes in Marking Pheromones of Bumblebees and Cuckoo Bumblebees," Chirality, 2004, pp. 228-233, vol. 16, No. 4.
Sonja Mayer et al., "Asymmetric Counteranion-Directed Catalysis," Angew. Chem. Int. Ed., 2006, pp. 4193-4195, vol. 45, No. 25.
International Searching Authority, nternational Search Report of PCT/JP2013/074108 dated Nov. 26, 2013.

*Primary Examiner* — Sikarl Witherspoon
(74) *Attorney, Agent, or Firm* — Sughrue Mion, PLLC

(57) ABSTRACT

A method for producing an optically active 2,3-dihydrofarnesal of formula (1) is disclosed. The method includes subjecting β-farnesene f formula (2) to amination in the presence of a lithium salt of an amine to obtain (2E)-farnesyl allylamine of general formula (3); subjecting the (2E)-farnesyl allylamine to asymmetric isomerization to obtain an optically active farnesyl enamine of general formula (4); and subjecting the optically active farnesyl enamine to solvolysis:

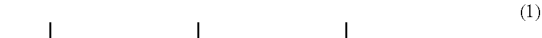

(1)

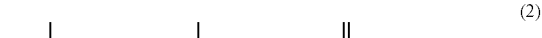

(2)

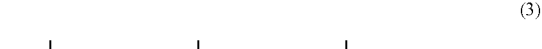

(3)

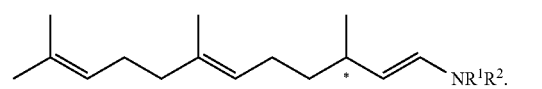

(4)

2 Claims, No Drawings

METHOD FOR PRODUCING OPTICALLY ACTIVE 2,3-DIHYDROFARNESAL

CROSS REFERENCE TO RELATED APPLICATIONS

This is a National Stage of International Application No. PCT/JP2013/074108 filed Sep. 6, 2013, claiming priority based on Japanese Patent Application No. 2012-197450 filed Sep. 7, 2012, the contents of all of which are incorporated herein by reference in their entirety.

TECHNICAL FIELD

The present invention relates particularly to a method for producing an optically active 2,3-dihydrofarnesal in a short process, which is economically advantageous. Specifically, the present invention relates to a method for producing an optically active 2,3-dihydrofarnesal in which the diene moiety of β-farnesene is subjected to selective amination to obtain (2E)-dihydrofarnesyl allylamine, the obtained (2E)-dihydrofarnesyl allylamine is subjected to asymmetric isomerization to obtain an optically active dihydrofarnesyl enamine, and the obtained optically active dihydrofarnesyl enamine is subjected to solvolysis to obtain the optically active 2,3-dihydrofarnesal.

BACKGROUND ART 2,3-Dihydrofarnesal is known as a flavor and/or fragrance substance characterized in an aroma with a floral note (Japanese Patent Application Publication No. Hei 8-3092). 2,3-Dihydrofarnesal is known to be present in animals and plants in the natural world. For example, 2,3-Dihydrofarnesal is known to be present in an extract of Orchids (*Aerides jarckianum*), flower scent components of *Citrus limon* (Phytochemical Analysis (1997), 8(4), pp. 159-166), pheromone components of Bumblebees and Cuckoo Bumblebees (Chirality (2004), 16(4), pp. 228-233), and the like.

Moreover, 2,3-dihydrofarnesal also serves as an important raw material for (6E)-2,3-dihydrofarnesal, which has antimicrobial activity and which is useful as a muguet flavor and/or fragrance (Japanese Patent Application Publication No. Hei 8-245979).

As an example of synthesis of 2,3-dihydrofarnesal in an optically active form, a report is known in which (2E,6E)-farnesal is subjected to asymmetric hydrogen transfer reaction to synthesize (3R)-2,3-dihydrofarnesal (Angewnate Chemie, International Edition (2006), 45(25), pp. 4193-4195). Actually, however, (2Z,6E)-farnesal used as the raw material has to be separated and purified from a mixture of geometrical isomers, (2E,6E)-farnesal and (2Z,6E)-farnesal, by fine distillation. Furthermore, the asymmetric hydrogen transfer reaction of (2E,6E)-farnesal for obtaining the optically active 2,3-dihydrofarnesal requires an expensive and special asymmetric ligand.

Meanwhile, as an example of synthesis of 2,3-dihydrofarnesal in a racemic form, a report is known in which (2Z,6E)-dihydrofarnesyl allylamine is subjected to isomerization reaction using bis-(α,α'-diphenylphosphino)-o-xylylene as a ligand to obtain (6E)-dihydrofarnesyl enamine in a racemic form, which is subsequently hydrolyzed using acetic acid to synthesize (6E)-dihydrofarnesal (Japanese Patent Application Publication No. Sho 58-4748). However, in this conventional method, the ligand used for the reaction is not an optically active isomer. The report does not describe application to (2E,6E)-dihydrofarnesyl amine, which is a geometrical isomer, at all. Moreover, this report neither describes at all nor suggests which optically active isomer is formed by the isomerization reaction using an optically active isomer as the ligand in combination with the substrate, (2Z,6E)-isomer or (2E,6E)-isomer. Moreover, a method for obtaining (2Z,6E)-dihydrofarnesyl allylamine or the chemical purity thereof is not described. Hence, this report does not describe how to obtain (2Z,6E)-dihydrofarnesyl amine with a high chemical purity. Moreover, this report neither describes at all nor suggests how to obtain (2E,6E)-dihydrofarnesyl amine with a high chemical purity.

SUMMARY OF INVENTION

Under the above-described situation, an object of the present invention is to provide a method for producing an optically active 2,3-dihydrofarnesal with a high chemical purity and a high optical purity by a simple operation in a safe manner in a good yield. In addition, another object of the present invention is to provide a synthetic intermediate useful for obtaining an optically active 2,3-dihydrofarnesal with a high chemical purity and a high optical purity. Still another object of the present invention is to provide a method for efficiently producing a synthetic intermediate useful for obtaining an optically active 2,3-dihydrofarnesal.

The present inventors have conducted intensive study to achieve the above-described objects, and found that (2E)-dihydrofarnesyl allylamine can be obtained with an extremely high chemical purity by selective amination of the diene moiety of β-farnesene, and that an optically active dihydrofarnesyl enamine, which is a novel compound, can be produced by asymmetric isomerization of the above-described (2E)-dihydrofarnesyl allylamine. The present inventors have further conducted study, and found that this novel optically active dihydrofarnesyl enamine is chemically stable, and can be stored, as it is, and the targeted optically active 2,3-dihydrofarnesal can be obtained easily in a good yield with a high chemical purity and a high optical purity by the solvolysis of the optically active dihydrofarnesyl enamine. These findings have led to the completion of the present invention.

Specifically, the present invention includes the following:

[1] A method for producing an optically active 2,3-dihydrofarnesal represented by formula (1):

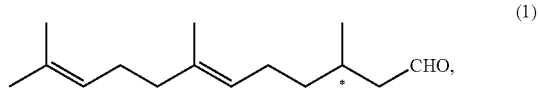 [SMILES: CC(C)=CCC/C(C)=C/CCC(C)CC=O]

(1)

wherein * represents an asymmetric carbon atom, the method comprising:

subjecting β-farnesene represented by formula (2) to amination in the presence of a lithium salt of an amine:

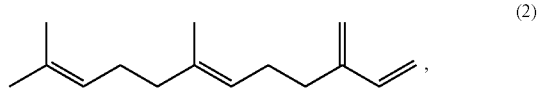

(2)

to obtain (2E)-farnesyl allylamine represented by general formula (3):

(3)

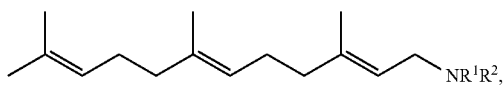

wherein R¹ and R² are each independently selected from the group consisting of a hydrogen atom, optionally substituted alkyl groups having 1 to 20 carbon atoms, optionally substituted 3- to 8-membered alicyclic groups, optionally substituted aryl groups having 6 to 15 carbon atoms, optionally substituted heterocyclic groups having 2 to 15 carbon atoms, and optionally substituted aralkyl groups having 7 to 12 carbon atoms, provided that R¹ and R² do not represent hydrogen atoms at the same time, or R¹ and R² may be bonded to each other to form a ring;

subsequently subjecting the (2E)-farnesyl allylamine to asymmetric isomerization to obtain an optically active farnesyl enamine represented by general formula (4):

(4)

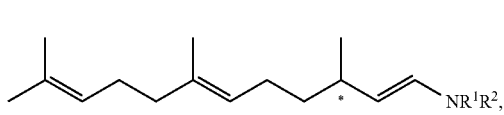

wherein R¹ and R² have the same meanings as defined above, and * represents an asymmetric carbon atom; and further subjecting the optically active farnesyl enamine to solvolysis.

[2] The production method according to the above-described [1], wherein the asymmetric isomerization is conducted by using a rhodium monocationic complex represented by general formula (5):

[Rh(olefin)L]⁺X⁻ (5), wherein the olefin is ethylene, 1,3-butadiene, cyclooctadiene, norbornadiene, or cycloocta-1,5-diene, X is $ClO_4$, $BF_4$, $PF_6$, or $PCl_6$, and L is an optically active bidentate phosphine ligand, or a rhodium dinuclear complex represented by general formula (6):

[Rh(L)₂]⁺X⁻ (6), wherein X and L have the same meanings as defined above.

[3] An optically active farnesyl enamine represented by general formula (4):

(4)

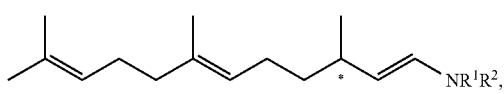

wherein R¹, R², and * are as defined in the above-described [1]. [4] The optically active farnesyl enamine according to the above-described [3], wherein the configuration of the optically active farnesyl enamine represented by general formula (4) is in the 3S-form.

[5] The optically active farnesyl enamine according to the above-described [3], wherein the configuration of the optically active farnesyl enamine represented by general formula (4) is in the 3R-form.

In the production method of the present invention, (2E)-dihydrofarnesyl allylamine can be obtained with a high chemical purity by the amination of β-farnesene conducted in the first step. For this reason, by using the (2E)-dihydrofarnesyl allylamine for the asymmetric isomerization in the subsequent step, an optically active dihydrofarnesyl enamine, which is a novel intermediate for producing an optically active 2,3-dihydrofarnesal, can be produced with an extremely high chemical purity and a high optical purity. In addition, in the case of the present invention, an optically active 2,3-dihydrofarnesal can be produced by solvolysis of the optically active dihydrofarnesyl enamine, which is the novel intermediate.

In addition, the novel optically active dihydrofarnesyl enamine of the present invention is useful as an intermediate for producing an optically active 2,3-dihydrofarnesol.

DESCRIPTION OF EMBODIMENTS

Hereinafter, a method for producing an optically active 2,3-dihydrofarnesal of the present invention will be described specifically.

The scheme of the method for producing an optically active 2,3-dihydrofarnesal of the present invention includes the reactions shown below:

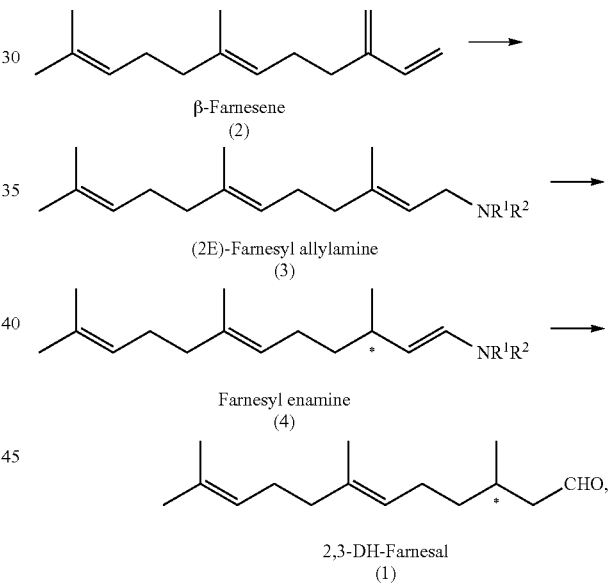

wherein R¹ and R² are each independently selected from the group consisting of a hydrogen atom, optionally substituted alkyl groups having 1 to 20 carbon atoms, optionally substituted 3- to 8-membered alicyclic groups, optionally substituted aryl groups having 6 to 15 carbon atoms, optionally substituted heterocyclic groups having 2 to 15 carbon atoms, and optionally substituted aralkyl groups having 7 to 12 carbon atoms, provided that R¹ and R² do not represent hydrogen atoms at the same time, or R¹ and R² may be bonded to each other to form a ring, and * represents an asymmetric carbon atom.

In other words, amination of β-farnesene represented by formula (2) is conducted in the presence of a lithium salt of an amine to obtain (2E)-farnesyl allylamine represented by general formula (3) with a high chemical purity. Subsequently, the (2E)-farnesyl allylamine is subjected to asymmetric isomerization to form the optically active farnesyl enamine represented by general formula (4). Further, by solvolysis of the optically active farnesyl enamine, the optically active 2,3-dihydrofarnesal represented by formula (1) can be obtained.

The amine which is a raw material for producing the optically active 2,3-dihydrofarnesal of the present invention is described.

The amine used in the present invention is represented by the following general formula (7):

$$HNR^1R^2 \qquad (7),$$

wherein $R^1$ and $R^2$ are each independently selected from the group consisting of a hydrogen atom, optionally substituted alkyl groups having 1 to 20 carbon atoms, optionally substituted 3- to 8-membered alicyclic groups, optionally substituted aryl groups having 6 to 15 carbon atoms, optionally substituted heterocyclic groups having 2 to 15 carbon atoms, and optionally substituted aralkyl groups having 7 to 12 carbon atoms, provided that $R^1$ and $R^2$ do not represent hydrogen atoms at the same time, or $R^1$ and $R^2$ may be bonded to each other to form a ring.

The alkyl group having 1 to 20 and preferably 1 to 10 carbon atoms represented by $R^1$ or R in general formula (7) may be linear or branched, and examples thereof include a methyl group, an ethyl group, a n-propyl group, an isopropyl group, a n-butyl group, an isobutyl group, a sec-butyl group, a tert-butyl group, a n-pentyl group, an iso-pentyl group, a neopentyl group, a hexyl group, a heptyl group, an octyl group, a nonyl group, a decyl group, an undecyl group, a dodecyl group, a tridecyl group, a tetradecyl group, a pentadecyl group, a hexadecyl group, a heptadecyl group, an octadecyl group, a nonadecyl group, an eicosyl group, and the like.

Examples of the 3- to 8-membered alicyclic group represented by $R^1$ or $R^2$ in general formula (7) include a cyclopropyl group, a cyclobutyl group, a cyclopentyl group, a cyclohexyl group, a cycloheptyl group, a cyclooctyl group, and the like.

Examples of the aryl group represented by $R^1$ or $R^2$ in general formula (7) include aryl groups having 6 to 15 carbon atoms such as aromatic monocyclic or polycyclic groups including a phenyl group, a naphthyl group, an anthryl group, a phenanthryl group, an indenyl group, and the like. Other examples include metallocenyl groups such as a ferrocenyl group.

The heterocyclic group represented by $R^1$ or $R^2$ in general formula (7) may be an aliphatic heterocyclic group or an aromatic heterocyclic group. Examples of the aliphatic heterocyclic group include 5- to 8-membered and preferably 5-or 6-membered monocyclic, polycyclic, or fused-cyclic aliphatic heterocyclic groups having 2 to 14 carbon atoms and at least one and preferably one to three heteroatoms such as nitrogen atoms, oxygen atoms, and sulfur atoms. Specific examples of the aliphatic heterocyclic groups include a 2-oxopyrrolidyl group, a piperidyl group, a piperazinyl group, a morpholino group, a tetrahydrofuryl group, a tetrahydropyranyl group, a tetrahydrothienyl group, and the like. Meanwhile, examples of the aromatic heterocyclic group include 5- to 8-membered and preferably 5- or 6-membered monocyclic, polycyclic, or fused-cyclic aromatic heterocyclic (heteroaryl) groups having 2 to 15 carbon atoms and at least one and preferably one to three heteroatoms such as nitrogen atoms, oxygen atoms, and sulfur atoms. Specific examples of the aromatic heterocyclic groups include a furyl group, a thienyl group, a pyridyl group, apyridinyl group, a pyrazinyl group, a pyridazinyl group, an imidazolyl group, an oxazolyl group, a thiazolyl group, a benzofuryl group, a benzothienyl group, a quinolyl group, an isoquinolyl group, a quinoxalinyl group, a phthalazinyl group, a quinazolinyl group, a naphthyridinyl group, a cinnolinyl group, a benzoimidazoline group, a benzoxazolyl group, a benzothiazolyl group, and the like.

The aralkyl group represented by $R^1$ or $R^2$ in general formula (7) may be, for example, an aralkyl group having 7 to 12 carbon atoms, and examples thereof include a benzyl group, a 1-phenylethyl group, a 2-phenylethyl group, and the like.

When $R^1$ and $R^2$ in general formula (7) are bonded to each other to form a ring, the ring may be a cyclic amine having 2 to 15 carbon atoms, and examples thereof include cyclic amines such as piperidine, pyrrolidine, morpholine, indoline, and isoindoline.

Here, the alkyl group represented by $R^1$ or $R^2$ may have a substituent(s), and the substituents include aryl groups, aralkyl groups, alicyclic groups, halogen atoms, hydroxyl groups, alkoxy groups, tri-substituted organosilyl groups, carboxyl groups, acyl groups, acyloxy groups, substituted amino groups, heterocyclic groups, nitro groups, and the like.

Likewise, the alicyclic group, aryl group, heterocyclic group, or aralkyl group represented by $R^1$ or $R^2$ may have a substituent (s), and the substituents include alkyl groups, aryl groups, aralkyl groups, alicyclic groups, halogen atoms, hydroxyl groups, alkoxy groups, tri-substituted organosilyl groups, carboxyl groups, acyl groups, acyloxy groups, substituted amino groups, heterocyclic groups, nitro groups, and the like.

Here, examples of the alkyl groups serving as the substituents include alkyl groups having 1 to 6 carbon atoms such as methyl groups, ethyl groups, n-propyl groups, isopropyl groups, sec-butyl groups, tert-butyl groups, pentyl groups, and hexyl groups.

Examples of the aryl groups serving as the substituents include aryl groups having 6 to 14 carbon atoms such as phenyl groups, α-naphthyl groups, β-naphthyl groups, anthryl groups, phenanthryl groups, and biphenyl groups.

The aralkyl groups serving as the substituents include aralkyl groups having 7 to 12 carbon atoms such as benzyl groups, 1-phenylethyl groups, 2-phenylethyl groups, α-naphthylmethyl groups, and β-naphthylmethyl groups.

The alicyclic groups serving as the substituents include alicyclic groups having 5 to 8 carbon atoms such as cyclopentyl groups, cyclohexyl groups, methylcyclohexyl groups, cycloheptyl groups, and cyclooctyl groups.

The halogen atoms serving as the substituents include fluorine atoms, chlorine atoms, bromine atoms, and iodine atoms.

The alkoxy groups serving as the substituents include alkoxy groups having 1 to 4 carbon atoms such as methoxy groups, ethoxy groups, n-propoxy groups, isopropoxy groups, n-butoxy groups, isobutoxy groups, sec-butoxy groups, and tert-butoxy groups.

The tri-substituted organosilyl groups serving as the substituents include tri(C1 to C6 alkyl)silyl groups such as trimethylsilyl groups, triethylsilyl groups, triisopropylsilyl groups, dimethylisopropylsilyl groups, diethylisopropylsilyl groups, dimethyl(2,3-dimethyl-2-butyl) silyl groups, tert-butyldimethylsilyl groups, and dimethylhexylsilyl groups.

The carboxyl groups serving as the substituents include alkoxycarbonyl groups having 2 to 6 carbon atoms such as methoxycarbonyl groups and ethoxycarbonyl groups and arylcarboxyl groups having 6 to 11 carbon atoms such as phenoxycarbonyl groups.

The acyl groups serving as the substituents include acyl groups having 1 to 8 carbon atoms such as formyl groups, acetyl groups, propironyl groups, n-butyroyl groups, isobutyroyl groups, and benzoyl groups.

The acyloxy groups serving as the substituents include acyloxy groups having 1 to 8 carbon atoms such as formyloxy groups, acyloxy groups, propionyloxy groups, n-butyroyloxy groups, isobutyroyloxy groups, and benzoyloxy groups.

The substituted amino groups serving as the substituents include dialkylamino groups having alkyl groups having 1 to 12 carbon atoms as substituents, such as dimethylamino groups, diethylamino groups, diisopropylamino groups, piperidyl groups, and piperidyl groups.

The heterocyclic groups serving as the substituents include aliphatic heterocyclic groups and aromatic heterocyclic groups. Examples of the aliphatic heterocyclic groups include 5- to 8-membered and preferably 5- or 6-membered monocyclic, polycyclic, or fused-cyclic aliphatic heterocyclic groups having 2 to 14 carbon atoms and at least one and preferably one to three heteroatoms such as nitrogen atoms, oxygen atoms, and sulfur atoms. Specific examples of the aliphatic heterocyclic groups include 2-oxopyrrolidyl groups, piperidyl groups, piperazinyl groups, morpholino groups, tetrahydrofuryl groups, tetrahydropyranyl groups, tetrahydrothienyl groups, and the like. Meanwhile, examples of the aromatic heterocyclic groups include 5- to 8-membered and preferably 5- or 6-membered monocyclic, polycyclic, or fused-cyclic aromatic heterocyclic (heteroaryl) groups having 2 to 15 carbon atoms and at least one and preferably one to three heteroatoms such as nitrogen atoms, oxygen atoms, and sulfur atoms. Specific examples of the aromatic heterocyclic groups include furyl groups, thienyl groups, pyridyl groups, pyridinyl groups, pyrazinyl groups, pyradizinyl groups, imidazolyl groups, oxazolyl groups, thiazolyl groups, benzofuryl groups, benzothienyl groups, quinolyl groups, isoquinolyl groups, quinoxalinyl groups, phthalazinyl groups, quinazolinyl groups, naphthyridinyl groups, cinnolinyl groups, benzoimidazoline groups, benzooxazolyl groups, benzothiazolyl groups, and the like.

Specific examples of the amine used in the present invention include dimethylamine, diethylamine, di-n-propylamine, diisopropylamine, cyclohexylamine, cyclohexylamine, piperidine, pyrrolidine, morpholine, and the like.

The amount of β-farnesene used relative to the amine is such that the amount of moles of β-farnesene is 1 to 100 times and preferably 1 to 10 times that of the amine.

The lithium salt of an amine used in the present invention can be obtained by reacting the amine with a lithium catalyst. As the lithium catalyst, an organic lithium compound or lithium metal can be used.

The lithium salt of an amine used in the present invention can be obtained by reacting an organic lithium compound with an amine. The lithium salt of an amine used in the present invention can also be prepared by a method in which lithium metal is reacted with an amine in the presence of a hydrogen acceptor olefin such as isoprene or styrene, or other methods. Any of these methods can be employed.

Here, the organic lithium compound includes methyllithium, n-butyllithium, sec-butyllithium, t-butyllithium, phenyllithium, and the like.

The amount of moles of the lithium catalyst used in the amination is 0.001 to 1 time and preferably 0.05 to 0.5 times that of the amine used for the reaction.

The amination reaction is conducted in an inert atmosphere with or without a solvent. When a solvent is used, a solvent capable of dissolving the lithium catalyst is used. Usable solvents include hydrocarbon solvents such as benzene and toluene, ether solvents such as tetrahydrofuran, and the like. The reaction temperature can be determined, as appropriate, by a person skilled in the art according to the raw material and reagent used, and is generally 0 to 150° C. and preferably 50 to 100° C.

The reaction time can be determined, as appropriate, by a person skilled in the art, and is generally several minutes to 24 hours, and preferably 1 to 10 hours.

(2E)-Farnesyl allylamine (3) can be obtained from the mixture of the amination reaction of β-farnesene (2) conducted under the above-described reaction conditions in the presence of the lithium salt of the amine as follows. Specifically, after completion of the reaction, the lithium catalyst serving as the catalyst is inactivated by adding water, ethanol, carbon dioxide, or the like. Then, the oil layer is subjected to a purification process by, for example, distillation, column chromatography, or the like.

The farnesyl allylamine is a compound having (2E)- and (2Z)-isomers. In the farnesyl allylamine obtained by the synthetic method of the present invention, however, (2E)-farnesyl allylamine (3), which is the (2E)-isomer, has an extremely high chemical purity with the (2E)-isomer/(2Z)-isomer ratio being 99/1 to 100/0. The (2E)-farnesyl allylamine (3) may be used for the asymmetric isomerization in the subsequent step without fine distillation.

An optically active farnesyl enamine (4) can be obtained by asymmetric isomerization of the (2E)-farnesyl allylamine (3) obtained by the above-described amination reaction.

As a method for asymmetric isomerization of the (2E)-farnesyl allylamine (3), a method for isomerization using an optically active transition metal complex as a catalyst can be employed.

As the optically active transition metal complex used in the present invention, a complex containing a transition metal complex and an optically active ligand is preferably used.

The ligand used in the optically active transition metal complex for the asymmetric isomerization of the (2E)-farnesyl allylamine (3) of the present invention may be a monodentate ligand, a polydentate ligand, or the like, and is preferably an optically active bidentate phosphine ligand.

The optically active bidentate phosphine ligand includes optically active bidentate phosphine ligands represented by the following general formula (8):

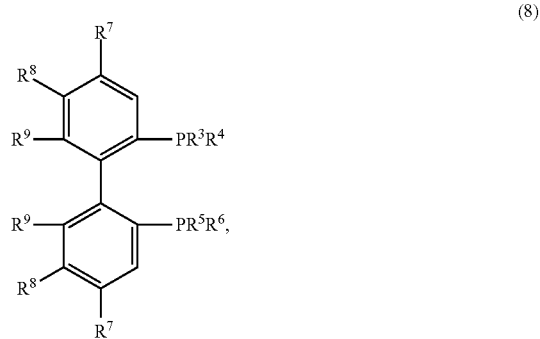

wherein $R^3$ to $R^6$ each independently represent an optionally substituted aromatic group having 6 to 15 carbon atoms or an optionally substituted cycloalkyl group having 3 to 10 carbon atoms, or each of the pairs of $R^3$ and $R^4$ and $R^5$ and $R^6$ may form a heterocycle together with the adjacent phosphorus atom; $R^7$ and $R^8$ each independently represent a hydrogen atom, an alkyl group having 1 to 5 carbon atoms, an alkoxy group having 1 to 5 carbon atoms, a di(C1 to C5 alkyl)amino group, a 5- to 8-membered cyclic amino group, or a halogen atom; and $R^9$ represents an alkyl group having 1 to 5 carbon atoms, an alkoxy group having 1 to 5 carbon atoms, a di(C1 to C5 alkyl)amino group, a 5- to 8-membered cyclic amino group, or a halogen atom; or each of the pairs of $R^7$ and $R^8$ and $R^8$ and $R^9$ may together form a condensed benzene ring, a condensed substituted benzene ring, a trimethylene group, a tetramethylene group, a pentamethylene group, a methylenedioxy group, an ethylenedioxy group, or a trimethylenedioxy group.

In general formula (8), $R^3$ to $R^6$ each independently represent an optionally substituted aromatic group having 6 to 15 carbon atoms or an optionally substituted cycloalkyl group having 3 to 10 carbon atoms, or each of the pairs of $R^3$ and $R^4$ and $R^5$ and $R^6$ may form a heterocycle together with the adjacent phosphorus atom.

The aromatic group in the optionally substituted aromatic group includes hydrocarbon-based aromatic groups such as a phenyl group, a naphthyl group, and a phenanthryl group; heteroaromatic groups such as a pyrrolyl group, a pyridyl group, a pyrazyl group, a quinolyl group, an isoquinolyl group, and an imidazolyl group; and the like.

Here, specific examples of the substituents include alkyl groups having 1 to 12 carbon atoms such as methyl groups, ethyl groups, n-propyl groups, isopropyl groups, n-butyl groups, isobutyl groups, sec-butyl groups, tert-butyl groups, n-pentyl groups, isopentyl groups, neopentyl groups, hexyl groups, heptyl groups, octyl groups, nonyl groups, decyl groups, undecyl groups, and dodecyl groups; lower alkoxy groups having 1 to 4 carbon atoms such as methoxy groups, ethoxy groups, n-propoxy groups, isopropoxy groups, n-butoxy groups, isobutoxy groups, sec-butoxy groups, and tert-butoxy group; aryl groups having 6 to 15 carbon atoms such as phenyl groups, α-naphthyl groups, β-naphthyl groups, and phenanthryl groups; aralkyl groups having 7 to 13 carbon atoms such as benzyl groups, α-phenylethyl groups, β-phenylethyl groups, α-phenylpropyl groups, β-phenylpropyl groups, γ-phenylpropyl groups, and naphthylmethyl groups; tri-substituted organosilyl groups including tri(C1 to C6 alkyl)silyl groups such as trimethylsilyl groups, triethylsilyl groups, triisopropylsilyl groups, dimethylisopropylsilyl groups, diethylisopropylsilyl groups, dimethyl(2,3-dimethyl-2-butyl) silyl groups, tert-butyldimethylsilyl groups, and dimethylhexylsilyl groups, di(C1 to C6 alkyl)-(C6 to C18 aryl)silyl groups such as dimethylcumylsilyl groups, di(C6 to C18 aryl)-(C1 to C6 alkyl)silyl groups such as tert-butyldiphenylsilyl groups and diphenylmethylsilyl groups, tri(C6 to C18 aryl)silyl groups such as triphenylsilyl groups, tri(C7 to 19 aralkyl)silyl groups such as tribenzylsilyl groups and tri-p-xylylsilyl groups, and the like; halogen atoms such as fluorine, chlorine, bromine, and iodine atoms; nitro groups; and the like.

Specific examples of the cycloalkyl group in the optionally substituted cycloalkyl group having 3 to 10 carbon atoms include a cyclopentyl group, a cyclobutyl group, a cyclopentyl group, a cyclohexyl group, a cycloheptyl group, a cyclooctyl group, a cyclononyl group, a cyclodecyl group, an octahydronaphthyl group, and the like.

Here, specific examples of the substituents include alkyl groups having 1 to 12 carbon atoms such as methyl groups, ethyl groups, n-propyl groups, isopropyl groups, n-butyl groups, isobutyl groups, sec-butyl groups, tert-butyl groups, n-pentyl groups, isopentyl groups, neopentyl groups, hexyl groups, heptyl groups, octyl groups, nonyl groups, decyl groups, undecyl groups, and dodecyl groups; lower alkoxy groups having 1 to 4 carbon atoms such as methoxy groups, ethoxy groups, n-propoxy groups, isopropoxy groups, n-butoxy groups, isobutoxy groups, sec-butoxy groups, and tert-butoxy group; aryl groups having 6 to 15 carbon atoms such as phenyl groups, α-naphthyl groups, β-naphthyl groups, and phenanthryl groups; aralkyl groups having 7 to 13 carbon atoms such as benzyl groups, α-phenylethyl groups, β-phenylethyl groups, α-phenylpropyl groups, β-phenylpropyl groups, γ-phenylpropyl groups, and naphthylmethyl groups; tri-substituted organosilyl groups including tri(C1 to C6 alkyl) silyl groups such as trimethylsilyl groups, triethylsilyl groups, triisopropylsilyl groups, dimethylisopropylsilyl groups, diethylisopropylsilyl groups, dimethyl(2,3-dimethyl-2-butyl) silyl groups, tert-butyldimethylsilyl groups, and dimethylhexylsilyl groups, di(C1 to C6 alkyl)-(C6 to C18 aryl)silyl groups such as dimethylcumylsilyl groups, di(C6 to C18 aryl)-(C1 to C6 alkyl) silyl groups such as tert-butyldiphenylsilyl groups and diphenylmethylsilyl groups, tri(C6 to C18 aryl) silyl groups such as triphenylsilyl groups, tri(C7 to 19 aralkyl) silyl groups such as tribenzylsilyl group and tri-p-xylylsilyl group, and the like; halogen atoms such as fluorine, chlorine, bromine, and iodine atoms; nitro groups; and the like.

In a case where any of the pairs of $R^3$ and $R^4$ and $R^5$ and $R^6$ forms a heterocycle together with the adjacent phosphorus atom, specific examples of the heterocyclic include phosphole, tetrahydrophosphole, phosphorinane, and the like. The heterocycle may have 1 to 4 functional groups which are inactive in the reaction of the present invention as substituents. Examples of the substituents include alkyl groups having 1 to 4 carbon atoms, alkoxy groups having 1 to 4 carbon atoms, halogen atoms, and the like.

$R^7$ and $R^8$ in general formula (8) are each independently a hydrogen atom, an alkyl group having 1 to 5 carbon atoms, an alkoxy group having 1 to 5 carbon atoms, a di(C1 to C5 alkyl) amino group, a 5- to 8-membered cyclic amino group, or a halogen atom.

Specific examples of the alkyl group having 1 to 5 carbon atoms represented by $R^7$ or $R^8$ include a methyl group, an ethyl group, a n-propyl group, an isopropyl group, a n-butyl group, an isobutyl group, a sec-butyl group, a tert-butyl group, a pentyl group, and the like.

Specific examples of the alkoxy group having 1 to 5 carbon atoms represented by $R^7$ or $R^8$ include a methoxy group, an ethoxy group, a n-propoxy group, an isopropoxy group, a n-butoxy group, an isobutoxy group, a sec-butoxy group, a tert-butoxy group, a pentoxy group, and the like.

Specific examples of the di(C1 to C5 alkyl) amino group represented by $R^7$ or $R^8$ include a dimethylamino group, a diethylamino group, a di-n-propylamino group, a diisopropylamino group, a di-n-butylamino group, a diisobutylamino group, a di-sec-butylamino group, a di-tert-butylamino group, a dipentylamino group, and the like.

Specific examples of the 5- to 8-membered cyclic amino group represented by $R^7$ and $R^8$ include a pyrrolidino group, a piperidino group, and the like.

Specific examples of the halogen atom represented by $R^7$ and $R^8$ include fluorine, chlorine, bromine, and iodine atoms, and the like.

Of these, $R^7$ and $R^8$ are each preferably a hydrogen atom; an alkyl group having 1 to 4 carbon atoms such as a methyl group, an ethyl group, a propyl group, an isopropyl group, a n-butyl group, a tert-butyl group, or a trifluoromethyl group; an alkoxy group such as a methoxy group, an ethoxy group, a n-propoxy group, an isopropoxy group, a n-butoxy group, or a tert-butoxy group; a dialkylamino group such as a dimethylamino group or a diethylamino group; a 5- to 8-membered cyclic amino group such as a pyrrolidino group or a piperidino group; or the like.

$R^7$ and $R^8$ are each particularly preferably a hydrogen atom or a methoxy group.

$R^9$ in general formula (8) is each independently an alkyl group having 1 to 5 carbon atoms, an alkoxy group having 1 to 5 carbon atoms, a di(C1 to C5 alkyl) amino group, a 5- to 8-membered cyclic amino group, or a halogen atom.

Specific examples of the alkyl group having 1 to 5 carbon atoms represented by $R^9$ include a methyl group, an ethyl group, a n-propyl group, an isopropyl group, a n-butyl group, an isobutyl group, a sec-butyl group, a tert-butyl group, a pentyl group, and the like.

Specific examples of the alkoxy group having 1 to 5 carbon atoms represented by $R^9$ include a methoxy group, an ethoxy group, a n-propoxy group, an isopropoxy group, a n-butoxy group, an isobutoxy group, a sec-butoxy group, a tert-butoxy group, a pentoxy group, and the like.

Specific examples of the di(C1 to C5 alkyl) amino group represented by $R^9$ include a dimethylamino group, a diethylamino group, a di-n-propylamino group, a diisopropylamino group, a di-n-butylamino group, a diisobutylamino group, a di-sec-butylamino group, a di-tert-butylamino group, a dipentylamino group, and the like.

Specific examples of the 5- to 8-membered cyclic amino group represented by $R^9$ include a pyrrolidino group, a piperidino group, and the like.

Specific examples of the halogen atom represented by $R^9$ include fluorine, chlorine, bromine, and iodine atoms, and the like.

Of these, $R^9$ is preferably an alkyl group having 1 to 4 carbon atoms such as a methyl group, an ethyl group, a propyl group, an isopropyl group, a n-butyl group, a tert-butyl group, or a trifluoromethyl group; an alkoxy group such as a methoxy group, an ethoxy group, a n-propoxy group, an isopropoxy group, a n-butoxy group, or a tert-butoxy group; a dialkylamino group such as a dimethylamino group or a diethylamino group; a 5- to 8-membered cyclic amino group such as a pyrrolidino group or a piperidino group; or the like.

$R^9$ is particularly preferably a methyl group or a methoxy group.

In general formula (8), each of the pairs of $R^7$ and $R^8$ and $R^8$ and $R^9$ may together form a condensed benzene ring, a condensed substituted benzene ring, a trimethylene group, a tetramethylene group, a pentamethylene group, a methylenedioxy group, an ethylenedioxy group, or a trimethylenedioxy group. Of these, it is preferable that $R^8$ and $R^9$ together form a condensed benzene ring, a condensed substituted benzene ring, a trimethylene group, a tetramethylene group, a pentamethylene group, a methylenedioxy group, an ethylenedioxy group, or a trimethylenedioxy group. It is particularly preferable that $R^8$ and $R^9$ together form a condensed benzene ring, a condensed substituted benzene ring, a tetramethylene group, a methylenedioxy group, a methylenedioxy group, or an ethylenedioxy group.

In addition, the condensed benzene ring, condensed substituted benzene ring, trimethylene group, tetramethylene group, pentamethylene group, methylenedioxy group, ethylenedioxy group, or trimethylenedioxy group may have, as substituents, functional groups which are inactive in asymmetric synthesis reaction. The number of the functional groups is preferably in the range of 0 to 4. Here, examples of the substituents include alkyl groups having 1 to 4 carbon atoms such as methyl groups, ethyl groups, n-propyl groups, isopropyl groups, n-butyl groups, isobutyl groups, sec-butyl groups, and tert-butyl groups; hydroxyl groups; alkoxy groups having 1 to 4 carbon atoms such as methoxy groups, ethoxy groups, n-propoxy groups, isopropoxy groups, n-butoxy groups, isobutoxy groups, sec-butoxy groups, and tert-butoxy group; halogen atoms such as fluorine, chlorine, bromine, and iodine atoms; and the like.

Examples of optically active bidentate phosphine ligands preferably used in general formula (8) include tertiary phosphines described in Japanese Patent Application Publication No. Sho 58-4749, Japanese Patent Application Publication No. Sho 61-63690, or Japanese Patent Application Publication No. Sho 62-265293. Specific examples thereof are as follows: 2,2'-bis(diphenylphosphino)-1,1'-binaphthyl (BINAP), 2,2'-bis(di(p-tolylphosphino)-1,1'-binaphthyl (Tol-BINAP), 2,2'-bis(di(3,5-xylyl)phosphino)-1,1'-binaphthyl (DM-BINAP), 2,2'-bis(di(3,5-di-tert-butylphenyl)phosphino)-1,1'-binaphthyl (T-Bu-2-BINAP), 2,2'-bis [di(4-methoxy-3,5-dimethylphenyl)phosphino]-1,1'-binaphthyl (DMM-BINAP), 2,2'-bis(dicyclohexylphosphino)-1,1-binaphthyl (Cy-BINAP), and 2,2'-bis(dicyclopentylphosphino)-1,1'-binaphthyl (Cp-BINAP).

Further, examples of optically active bidentate phosphine ligands preferably used in general formula (8) also include tertiary phosphines described in Japanese Patent Application Publication No. Hei 4-139140. Specific examples thereof are as follows: 2,2'-bis(diphenylphosphino)-5,5',6,6',7,7',8,8'-octahydrobinaphthyl (H8-BINAP), 2,2'-bis(di-p-tolylphosphino)-5,5',6,6',7,7',8,8'-octahydro binaphthyl (Tol-H8-BINAP), 2,2'-bis(di-(3,5-xylyl)phosphino)-5,5',6,6',7,7',8,8'-octahydrobinaphthyl (DM-H8-BINAP), and 2,2'-bis(di-(4-methoxy-3,5-dimethylphenyl)phosphino)-5,5',6,6',7,7',8,8'-octahydrobinaphthyl (DMM-H8-BINAP).

Moreover, examples of optically active bidentate phosphine ligands preferably used in general formula (8) also include tertiary phosphines described in Japanese Patent Application Publication No. Hei 11-269185. Specific examples thereof are as follows: ((5,6), (5',6')-bis(methylenedioxy)biphenyl-2,2'-diyl)bis(di phenylphosphine) (SEGPHOS), ((5,6), (5',6')-bis(methylenedioxy)biphenyl-2,2'-diyl)bis(di-p-tolylphosphine) (Tol-SEGPHOS), ((5,6), (5', 6')-bis(methylenedioxy)biphenyl-2,2'-diyl)bis(di-3,5-xylylphosphine) (DM-SEGPHOS), ((5,6), (5',6')-bis(methylenedioxy)biphenyl-2,2'-diyl)bis(di-4-methoxy-3,5-dimethylphenylphosphine) (DMM-SEGPHOS), ((5,6), (5', 6')-bis(methylenedioxy)biphenyl-2,2'-diyl)bis(di-4-methoxy-3,5-di-tert-butylphenylphosphine) (DTBM-SEGPHOS), and ((5,6), (5',6')-bis(methylenedioxy) biphenyl-2,2'-diyl)bis(di cyclohexylphosphine) (Cy-SEGPHOS).

In addition to the above-described optically active bidentate phosphine ligands, optically active bidentate phosphine ligands which may be represented by general formula (8) are as follows: 2,2'-dimethyl-6,6'-bis(diphenylphosphino)-1,1'-biphenyl (BIPHEMP), 2,2'-dimethyl-6,6'-bis(di-p-tolylphosphino)-1,1'-biphenyl (Tol-BIPHEMP), 2,2'-dimethyl-6,6'-bis (di-3,5-xylylphosphino)-1,1'-biphenyl (DM-BIPHEMP), 2,2'-dimethyl-6,6'-bis(di-4-methoxy-3,5-dimethylphenylphosphino)-1,1'-biphenyl (DMM-BIPHEMP), 2,2'-dimethyl-6,6'-bis(di-4-t-butoxy-3,5-dimethylphenylphosphino)-1,1'-biphenyl (DTBM-BIPHEMP), 2,2'-dimethyl-6,6'-bis (dicyclohexylphosphino)-1,1'-biphenyl (Cy-BIPHEMP), 2,2'-dimethoxy-6,6'-bis(diphenylphosphino)-1,1'-biphenyl (MeO-BIPHEP), 2,2'-dimethoxy-6,6'-bis(di-p-tolylphosphino)-1,1'-biphenyl (Tol-MeO-BIPHEP), 2,2'-dimethoxy-6,6'-bis(di-3,5-xylylphosphino)-1,1'-biphenyl (DM-MeO-BIPHEP), 2,2'-dimethoxy-6,6'-bis(di-4-methoxy-3,5-dimethylphenylphosphino)-1,1'-biphenyl (DMM-MeO-BIPHEP), 2,2'-dimethoxy-6,6'-bis(di-4-t-butoxy-3,5-dimethylphenylphosphino)-1,1'-biphenyl (DTBM-MeO-BIPHEP), 2,2'-dimethoxy-6,6'-bis(dicyclohexylphosphino)-1,1'-biphenyl (Cy-MeO-BIPHEP), 2,2'-dimethyl-3,3'- dichloro-4,4'-dimethyl-6,6'-bis(di-p-tolylphosphino)-1,1'-biphenyl (Tol-CM-BIPHEMP), 2,2'-dimethyl-3,3'-dichloro-4,4'-dimethyl-6,6'-bis(di-3,5-xylylphosphino)-1,1'-biphenyl (DM-CM-BIPHEMP), and 2,2'-dimethyl-3,3'-dichloro-4,4'-dimethyl-6,6'-bis(di-4-methoxy-3,5-dimethylphenylphosphino)-1,1'-biphenyl (DMM-CM-BIPHEMP).

In the present invention, an asymmetric hydrogenation reaction can be conducted by using an optically active transition metal complex comprising the above-described optically active bidentate phosphine ligand and a transition metal. Examples of the optically active transition metal complex preferable for this asymmetric hydrogenation reaction include optically active rhodium complexes represented by general formula (5) and general formula (6):

$$[Rh(olefin)L]^+X^- \quad (5),$$

wherein the olefin is ethylene, 1,3-butadiene, cyclooctadiene, norbornadiene, or cycloocta-1,5-diene, X is $ClO_4$, $BF_4$, $PF_6$, or $PCl_6$, and L is an optically active bidentate phosphine ligand, or

$$[Rh(L)_2]^+X^- \quad (6),$$

wherein X and L have the same meanings as defined above.

A method for producing the optically active rhodium complex represented by general formula (5) or general formula (6) is not particularly limited, and the optically active rhodium complex can be produced by, for example, the method shown below or a method based on the method shown below. Note that, in the formulae of transition metal-phosphine complexes shown below, cod represents cycloocta-1,5-diene, and nbd represents norbornadiene.

A specific example of production of the optically active rhodium complex is as follows. Specifically, the optically active rhodium complex can be synthesized by reacting chloro(1,5-cyclooctadiene)rhodium(I) dimer ($[Rh(cod)Cl]_2$) silver perchlorate, and the above-described optically active bidentate phosphine ligand with each other according to any of the methods described in Japanese Patent Application Publication No. Sho 58-4748, Japanese Patent Application Publication No. Sho 59-20294, and Japanese Patent Application Publication No. Sho 60-61587.

Specific examples of the rhodium complex are shown below.

The optically active rhodium complexes represented by general formula (5) are as follows: [Rh(cod)(L)]OTf, [Rh(cod)(L)]$BF_4$, [Rh(cod)(L)]$ClO_4$, [Rh(cod)(L)]$SbF_6$, [Rh(cod)(L)]$PF_6$, [Rh(cod)(L)]$BPh_4$, [Rh(nbd)(L)]OTf, [Rh(nbd)(L)]$BF_4$, [Rh(nbd)(L)]$ClO_4$, [Rh(nbd)(L)]$SbF_6$, [Rh(nbd)(L)]$PF_6$, and [Rh(nbd)(L)]$BPh_4$.

The optically active rhodium complexes represented by general formula (6) are as follows: [Rh(L)$_2$]OTf, [Rh(L)$_2$]$BF_4$, [Rh(L)$_2$]$ClO_4$, [Rh(L)$_2$]$SbF_6$, [Rh(L)$_2$]$PF_6$, and [Rh(L)$_2$]$BPh_4$.

Each of the optically active bidentate phosphine ligands exist in the (S)-form and the (R)-form. It is only necessary to select one of these forms according to the desired absolute configuration of the optically active farnesyl enamine (3). Specifically, when the substrate in the (E)-form is used, and, for example, when Tol-BINAP is used as the ligand, Tol-BINAP in the (S)-form is used to obtain the optically active farnesyl enamine (4) in the (R)-form. Meanwhile, Tol-BINAP in the (R)-form is used to obtain the optically active farnesyl enamine (4) in the (S)-form. On the other hand, when the substrate in the (Z)-form is used, Tol-BINAP in the (R)-form is used to obtain the optically active farnesyl enamine (4) in the (S)-form, whereas Tol-BINAP in the (S)-form is used to obtain the optically active farnesyl enamine (4) in the (R)-form.

Note that the amount of moles of the transition metal-optically active phosphine complex used is preferably approximately 1/100 to 1/50000 times that of the farnesyl allylamine (3).

In addition, any suitable solvent can be used as the reaction solvent, as long as the solvent is capable of dissolving the raw material and the catalyst system of the asymmetric hydrogenation. For example, it is possible to use aromatic hydrocarbon solvents such as toluene and xylene; aliphatic hydrocarbon solvents such as pentane and hexane; halogen-containing hydrocarbon solvents such as methylene chloride; ether solvents such as diethyl ether, diisopropyl ether, diethylene glycol dimethyl ether, tetrahydrofuran, and 1,3-dioxolane; alcohol solvents such as methanol, ethanol, 2-propanol, butanol, and benzyl alcohol; and heteroatom-containing organic solvents such as acetonitrile, DMF, and DMSO. It is preferable to use an ether solvent or a mixture solvent with an ether solvent. The amount of the solvent is determined based on the solubility of the reaction substrate and cost efficiency. For example, the reaction can be conducted in a range from a low concentration of 1% or lower to a nearly solventless state depending on the substrate. However, the reaction is preferably conducted by using the solvent in an amount of 0.1 to 5.0 times by volume. Regarding the reaction temperature, the reaction can be conducted at 0 to 150° C., and more preferably in a range from 70 to 120° C. In addition, the reaction time varies depending on reaction conditions such as the concentration of the reaction substrate, the temperature, and the pressure. The reaction is completed in several minutes to 30 hours. After completion of the reaction, the targeted optically active farnesyl enamine (4) can be isolated by ordinary post treatments.

The optically active farnesyl enamine (4) obtained by the above-described asymmetric isomerization is an unprecedented novel compound, which is stable, generally oily, and storable. For this reason, the optically active farnesyl enamine (4) obtained by the above-described addition reaction may be, for example, subjected to a purification process such as a distillation or column chromatography treatment. Alternatively, the optically active farnesyl enamine (4) may be stored without conducting any purification process, and taken out from a storage container before use in the subsequent step for production.

The optically active 2,3-dihydrofarnesal (1) can be obtained by solvolysis of the optically active farnesyl enamine (4) obtained by the above-described asymmetric isomerization.

As a method for the solvolysis, an ordinary known or well-known method for solvolysis of an enamine can be used. For example, a method may be used in which the reaction is conducted by using an acidic catalyst in a solvent. Examples of the acidic catalyst used in the solvolysis include hydrofluoric acid, hydrochloric acid, hydrobromic acid, sulfuric acid, phosphoric acid, methanesulfonic acid, p-toluenesulfonic acid, acetic acid, chloroacetic acid, trifluoroacetic acid, acidic ion-exchange resin, and the like. Preferred acidic catalysts include hydrochloric acid, sulfuric acid, p-toluenesulfonic acid, and the like, because these acidic catalysts are inexpensive and versatile and achieve a high reaction selectivity and a high reaction yield. One or a mixture of two or more of these acidic catalysts can be used, but a method using one of these acidic catalysts is preferable.

In addition, the solvent used for the solvolysis may be any, as long as the solvolysis proceeds in the solvent. Examples of the solvent include water, alcohols such as methanol, ethanol, and isopropanol, and the like, as well as mixture solvents thereof. Especially, methanol and ethanol are preferable, because they are inexpensive and versatile, and achieve a high reaction selectivity and high reaction yield.

Moreover, if necessary, an auxiliary solvent may be used. As the auxiliary solvent, any solvent may be used, as long as the solvent does not participate in the reaction. Examples of the auxiliary solvent include organic solvents including ether solvents such as diethyl ether, diisopropyl ether, tetrahydrofuran, dimethoxyethane, and dioxane, hydrocarbon solvents such as hexane, heptane, and octane, aromatic solvents such as benzene, toluene, and xylene, and the like.

Regarding the amount of the solvent used, the volume of the solvent is generally 0.5 to 100 times and preferably 1 to 30 times relative to 1 part by mass of the optically active farnesyl enamine (4). In addition, the reaction is conducted generally at a temperature of about 0 to 250° C. and preferably at a temperature of about 20 to 100° C., and the reaction is completed in generally about 10 minutes to 20 hours preferably about 30 minutes to 10 hours. These conditions can be modified, as appropriate, according to the solvent used and the amounts of the catalyst and the like.

After completion of the reaction, the target product can be isolated by ordinary post treatments by employing, if necessary, a method such as distillation or column chromatography. In addition, the reaction mode in the present invention may be batchwise or continuous.

Regarding the configuration of the asymmetric carbon atom at the 3-position of the optically active farnesyl enamine (4) in this reaction, the configuration of the optically active farnesyl enamine (4) is kept. For example, when (3R)-farnesyl enamine is used, (3R)-dihydrofarnesal can be obtained with the optical purity being kept. In other words, the configuration of the optically active 2,3-dihydrofarnesal is controlled by the configuration of the optically active ligand used in the asymmetric isomerization reaction.

EXAMPLES

Hereinafter, the present invention will be described more specifically on the basis of Examples. However, the present invention is not limited to these examples at all.

The analyses in Examples were conducted by using the following analytical instruments.

NMR measuring instrument: AVANCE III 500 model (500 MHz; manufactured by Bruker BioSpin K.K.)
[Mass Spectrometry and Chemical Purity]
Gas chromatograph-mass spectrometer: GCMS-QP2010 (manufactured by Shimadzu Corporation)
Column used: BC-WAX (50 m×0.25 mm ID; manufactured by GL Sciences Inc.)
Oven conditions: 70° C.-217° C., 4° C./min
[Optical Purity]
Gas chromatograph: GC-2010 (manufactured by Shimadzu Corporation)
Column used: BGB-174 (30 m×0.25 mm ID; manufactured by BGB Analytik AG)
Oven conditions: 90° C.-150° C., 0.4° C./min
Infrared absorption spectrum measuring instrument: FT/IR-6100 (manufactured by JASCO Corporation)
Window material: Sodium chloride
Polarimeter: P-1020 (manufactured by JASCO Corporation)

Example 1

Under a nitrogen atmosphere, 4.29 g (0.0587 mol) of diethylamine was placed in a 20-ml flask and stirred at 5° C. Subsequently, 3.7 ml (1.6 mol/L, 0.0587 mol) of an n-butyllithium hexane solution was added thereto, and the mixture was stirred at 5° C. for 10 minutes to form a lithium diethylamine solution.

A 30-ml pressure-resistant ampoule was purged with nitrogen, and 4.0 g (0.0196 mol) of β-farnesene (manufactured by Wako Pure Chemical Industries, Ltd.) was added thereto, followed by stirring at 15° C. for 10 minutes. Next, the lithium diethylamine solution was added over 5 minutes, and then the mixture was heated with stirring at 70° C. for 4 hours (conversion: 99% or higher).

After completion of the reaction, 40 ml of toluene was added, and then the mixture was washed with 8 ml of water. Subsequently, toluene was first removed by Claisen distillation, and then 4.48 g (GC chemical purity: 92.9% (2E,6E-isomer), 1.8% (2Z,6E-isomer), 4.16 g (0.015 mol)) of N,N-diethyl-3,7,11-trimethyldodeca-2E, 6E,10-trien-1-amine was obtained at a boiling point of 108 to 110° C./20 Pa in a yield of 77%.

Physical Data of
N,N-Diethyl-3,7,11-trimethyldodeca-2E,
6E,10-trien-1-amine

Molecular Weight = 277.50
Molecular Formula = C19H35N

NMR Data
$^1$H-NMR (500 MHz, CHLOROFORM-D): δ 1.03 (t, J=7.2 Hz, 3H×2), δ 1.60 (s, 3H×2), δ 1.64 (s, 3H), δ 1.68 (s, 3H), δ 1.95-2.15 (m, 2H×4), δ 2.51 (q, J=7.2 Hz, 2H×2), δ 3.06 (d, J=6.8 Hz, 2H), δ 5.10 (t, J=6.8 Hz, 1H), δ 5.11 (t, J=6.8 Hz, 1H), δ 5.27 (t, J=6.8 Hz, 1H)

$^{13}$C-NMR (125 MHz, CHLOROFORM-D): δ 11.86 (CH$_3$×2), 16.04 (CH$_3$), 16.36 (CH$_3$), 17.68 (CH$_3$), 25.70 (CH$_3$), 26.44 (CH$_2$), 26.79 (CH$_2$), 39.75 (CH$_2$), 39.85 (CH$_2$), 46.72 (CH$_2$×2), 50.57 (CH$_2$), 121.79 (CH), 124.08 (CH), 124.42 (CH), 131.28 (C), 135.11 (C), 137.68 (C)

Example 2

Under a nitrogen atmosphere, 24.7 mg (0.05 mmol) of chloro(1,5-cyclooctadiene)rhodium(I) dimer ([Rh(cod)Cl]$_2$ and 20.7 mg (0.1 mmol) of silver perchlorate (AgClO$_4$) were placed in a 20-ml flask having a branch, and 6 ml of tetrahydrofuran was added thereto with stirring, followed by stirring at 15° C. for 2 hours. Subsequently, 4 ml of a tetrahydrofuran solution containing 67.8 mg (0.1 mmol) of (S)-Tol-BINAP was added thereto, followed by stirring at 15° C. for 2 hours. Then, the silver chloride formed was removed by filtration, and the filtrate was used as a catalyst solution.

A 200-ml pressure-resistant ampoule was purged with nitrogen, and 5 ml (0.05 mmmol) of the rhodium complex catalyst solution and 2 ml of tetrahydrofuran were added thereto. Finally, 3.36 g (GC purity: 92.9%, 3.12 g, 11.25 mmol) of N,N-diethyl-3,7,11-trimethyldodeca-2E, 6E,10- trien-1-amine (obtained in Example 1) was added thereto, and the mixture was heated with stirring at 100° C. for 14 hours (conversion: 99% or higher).

After completion of the reaction, tetrahydrofuran was first removed by Claisen distillation, and then 2.65 g (GC purity: 93.5%, 0.915 g, 8.93 mmol) of (3R)—N,N-diethyl-3,7,11-trimethyldodeca-1,6E,10-trien-1-amine was obtained at a boiling point of 88 to 97° C./20 Pa in a yield of 79%.

Physical Data of (3R)—N,N-Diethyl-3,7,11-trimethyldodeca-1,6E,10-trien-1-amine

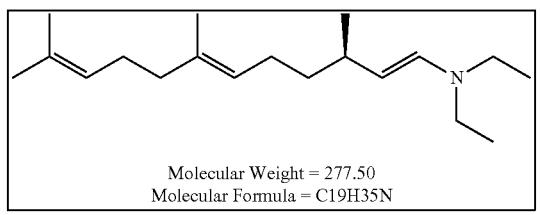 [SMILES: CCN(/C=C/[C@H](C)CC/C=C(\C)CCC=C(C)C)CC]

Molecular Weight = 277.50
Molecular Formula = C19H35N

NMR Data $^1$H-NMR (500 MHz, CHLOROFORM-D): δ 0.97 (d, J=6.7 Hz, 3H), δ 1.04 (t, J=7.1 Hz, 3H×2), δ 1.2-1.35 (m, 2H), δ 1.59 (s, 3H), δ 1.60 (s, 3H), δ 1.68 (s, 3H), δ 1.95-2.1 (m, 7H), δ 2.93 (q, J=7.1 Hz, 2H×2), δ 4.04 (dd, J=8.2, 13.9 Hz, 1H), δ 5.1 (m, 1H×2), δ 5.80 (d, J=13.9 Hz, 1H)

$^{13}$C-NMR (125 MHz, CHLOROFORM-D): δ 12.16 (CH$_3$×2), 15.96 (CH$_3$), 17.66 (CH$_3$), 22.73 (CH$_3$), 25.68 (CH$_3$), 25.95 (CH$_2$), 26.76 (CH$_2$), 34.99 (CH), 38.90 (CH$_2$), 39.77 (CH$_2$), 44.43 (CH$_2$×2), 105.07 (CH), 124.49 (CH), 125.15 (CH), 131.17 (C), 134.36 (C), 135.78 (CH) Infrared absorption spectrum (CCl$_4$: cm$^{-1}$): 2960, 1650, 1450, 1374, 1245, 1197, 1095, 935

EI-MS data (27 eV): 277 (M+; 5), 262 (5), 208 (50), 193 (5), 166 (5), 152 (5), 126 (100), 110 (5), 86 (20), 72 (15), 56 (15), 41 (15)

Specific rotation: $[\alpha]_D^{20}$ −36.8 (c 1.0, Pyridine)

Example 3

Under a nitrogen atmosphere, 24.7 mg (0.05 mmol) of chloro(1,5-cyclooctadiene)rhodium(I) dimer ([Rh(cod)Cl]$_2$ and 20.7 mg (0.1 mmol) of silver perchlorate (AgClO$_4$) were placed in a 20-ml flask having a branch, and 6 ml of tetrahydrofuran was added thereto with stirring, followed by stirring at 15° C. for 2 hours. Subsequently, 4 ml of a tetrahydrofuran solution containing 67.8 mg (0.1 mmol) of (R)-Tol-BINAP was added thereto, followed by stirring at 15° C. for 2 hours. Then, the silver chloride formed was removed by filtration, and the filtrate was used as a catalyst solution.

A 200-ml pressure-resistant ampoule was purged with nitrogen, and 2 ml (0.02 mmol) of the rhodium complex catalyst solution and 2 ml of tetrahydrofuran were added thereto. Finally, 1.12 g (GC purity: 92.9%, 1.04 g, 3.75 mmol) of N,N-diethyl-3,7,11-trimethyldodeca-2,6,10-trien-1-amine (obtained in Example 1) was added thereto, and the mixture was heated with stirring at 100° C. for 14 hours (conversion: 99% or higher).

After completion of the reaction, tetrahydrofuran was first removed by Claisen distillation, and then 1.00 g (GC purity: 91.5%, 0.915 g, 3.30 mmol) of (3S)—N,N-diethyl-3,7,11-trimethyldodeca-1,6E, 10-trien-1-amine was obtained at a boiling point of 88 to 94° C./20 Pa in a yield of 88%.

Physical Data of (3S)—N,N-Diethyl-3,7,11-trimethyldodeca-1,6E,10-trien-1-amine

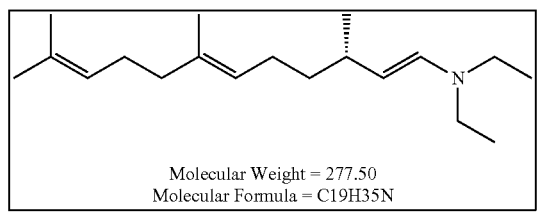 [SMILES: CCN(/C=C/[C@@H](C)CC/C=C(\C)CCC=C(C)C)CC]

Molecular Weight = 277.50
Molecular Formula = C19H35N

NMR Data $^1$H-NMR (500 MHz, CHLOROFORM-D): δ 0.97 (d, J=6.8 Hz, 3H), δ 1.04 (t, J=7.1 Hz, 3H×2), δ 1.2-1.35 (m, 2H), δ 1.59 (s, 3H), δ 1.60 (s, 3H), δ 1.68 (s, 3H), δ 1.95-2.1 (m, 7H), δ 2.93 (q, J=7.1 Hz, 2H×2), δ 4.04 (dd, J=8.1, 13.9 Hz, 1H), δ 5.1 (m, 1H×2), δ 5.79 (d, J=13.9 Hz, 1H)

$^{13}$C-NMR (125 MHz, CHLOROFORM-D): δ 12.16 (CH$_3$×2), 15.96 (CH$_3$), 17.66 (CH$_3$), 22.73 (CH$_3$), 25.68 (CH$_3$), 25.95 (CH$_2$), 26.76 (CH$_2$), 34.99 (CH), 38.90 (CH$_2$), 39.77 (CH$_2$), 44.43 (CH$_2$×2), 105.07 (CH), 124.49 (CH), 125.15 (CH), 131.17 (C), 134.36 (C), 135.78 (CH) Infrared absorption spectrum (CCl$_4$: cm$^{-1}$): 2960, 2924, 2865, 1650, 1450, 1374, 1245, 1197, 1095, 935

EI-MS data (27 eV): 277 (M+; 5), 262 (5), 208 (50), 193 (5), 166 (5), 152 (5), 126 (100), 110 (5), 86 (20), 72 (15), 56 (15), 41(15)

Specific rotation: $[\alpha]_D^{20}$ +36.1 (c 1.0, Pyridine)

Example 4

A 100 ml pressure-resistant ampoule was purged with nitrogen, and 1 ml (0.01 mmol) of the rhodium complex catalyst solution prepared in Example 3, and 2 ml of tetrahydrofuran were added thereto. Finally, 2.78 g (10 mmol, (GC purity: 59.3% (2E,6E-isomer), 22.2% (2Z,6E-isomer)) of N,N-diethyl-3,7,11-trimethyldodeca-2,6,10-trien-1-amine (obtained in Synthesis Example 1) was added thereto, and the mixture was heated with stirring at 100° C. for 16 hours. The reaction product was analyzed by gas chromatography. The results showed that the conversion of the 2E, 6E-isomer was 67.3%, whereas the 2Z, 6E-isomer had a poor reactivity with a conversion of 47.6%.

Synthesis Example 1

In a 300-ml flask, 100 g (1.0 mol) of concentrated hydrochloric acid was added, and stirred at 5° C. for 10 minutes. Subsequently, 55.6 g (0.25 mol) of 6E-nerolidol was added thereto over 30 minutes, followed by stirring at 5° C. for 3 hours. Subsequently, the mixture was neutralized with a 25% aqueous sodium hydroxide solution. Then, extraction was conducted with 100 ml of toluene, and then the aqueous layer was removed.

To a 300-ml flask, the obtained organic layer was added, and then 36.6 g (0.5 mol) of diethylamine was added over 10 minutes. Further, 26.5 g (0.25 mol) of sodium carbonate was added thereto, followed by stirring at 45° C. for 3 hours.

After completion of the reaction, 100 ml of toluene was added, and then the precipitates were removed by filtration. The obtained filtrate was washed twice with 50 ml of water, and then toluene was removed by an evaporator to obtain 28.6 g of a concentrate.

The obtained concentrate was subjected to silica column chromatography (silica gel: 300 g). First, impurities were removed with hexane:ethyl acetate=3:1, and then a fraction (13.0 g) rich in N,N-diethyl-3,7,11-trimethyldodeca-2,6,10-trien-1-amine was obtained using hexane:triethylamine=20:1. Subsequently, by Claisen distillation, 10.9 g (GC purity: 59.3% (2E,6E-isomer), 22.2% (2Z,6E-isomer)), 8.9 g, 0.032 mol) of N,N-diethyl-3,7,11-trimethyldodeca-2,6-10-trien-1-amine was obtained at a boiling point of 100 to 110° C./20 Pa in a yield of 13%.

Physical Data of N,N-Diethyl-3,7,11-trimethyl-dodeca-2Z,6E-10-triene

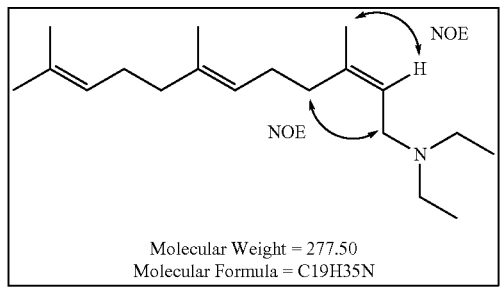 [SMILES: CCN(CC)C/C=C(/C)CC/C=C(\C)CCC=C(C)C]

Molecular Weight = 277.50
Molecular Formula = C19H35N

NMR Data $^1$H-NMR (500 MHz, CHLOROFORM-D): δ 1.03 (t, J=7.2 Hz, 3H×2), δ 1.60 (s, 3H×2), δ 1.68 (s, 3H), δ 1.73 (s, 3H), δ 1.95-2.15 (m, 2H×4), δ 2.50 (q, J=7.2 Hz, 2H×2), δ 3.05 (d, J=6.8 Hz, 2H), δ 5.05-5.15 (m, 1H×2), δ 5.24-5.29 (m, 1H) $^{13}$C-NMR (125 MHz, CHLOROFORM-D): δ 11.82 (CH$_3$×2), 15.99 (CH$_3$), 17.69 (CH$_3$), 23.59 (CH$_3$), 25.70 (CH$_3$), 26.52 (CH$_2$), 26.72 (CH$_2$), 32.20 (CH$_2$), 39.74 (CH$_2$), 46.69 (CH$_2$×2), 50.44 (CH$_2$), 122.66 (CH), 123.97 (CH), 124.35 (CH), 131.34 (C), 135.34 (C), 137.85 (C)

Example 5

To a 100-ml flask, 1.42 g (GC purity: 93.5%, 1.33 g, 4.78 mmol) of N,N-diethyl-3,7,11-trimethyldodeca-1,6,10-trien-1-amine (obtained in Example 2), 70 ml of toluene, and 15 ml of 1 N aqueous sulfuric acid were added, and stirred at 15° C. for 10 minutes (conversion: 99% or higher). After the aqueous layer was removed, the organic layer was washed twice with 30 ml of 10% sodium carbonate solution, and further washed twice with 30 ml of water.

After completion of the washing, first, toluene was removed by Claisen distillation, and then 1.07 g (GC purity: 99.5%, optical purity: 95% e.e., 1.06 g, 4.78 mmol) of (3R)-dihydrofarnesal was obtained at a boiling point of 68 to 72° C./20 Pa in a yield of 100%.

Physical Data of (3R)-Dihydrofarnesal

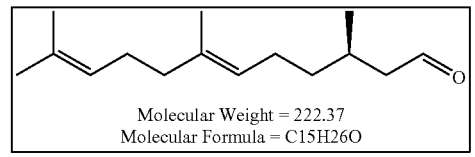 [SMILES: CC(C)=CCC/C(C)=C/CC[C@@H](C)CC=O]

Molecular Weight = 222.37
Molecular Formula = C15H26O

NMR Data $^1$H-NMR (500 MHz, CHLOROFORM-D): δ 0.98 (d, J=6.7 Hz, 3H), δ 1.25-1.4 (m, 2H), δ 1.60 (s, 3H×2), δ 1.68 (s, 3H), δ 1.95-2.1 (m, 7H), δ 2.23 (ddd, J=2.7, 8.0, 16.0 Hz, 1H), δ 2.41 (ddd, J=2.1, 5.6, 16.0 Hz, 1H), δ 5.1 (m, 1H×2), δ 9.76 (t, J=2.7 Hz, 1H)

$^{13}$C-NMR (125 MHz, CHLOROFORM-D): δ 15.96 (CH$_3$), 17.65 (CH$_3$), 19.87 (CH$_3$), 25.27 (CH$_2$), 25.66 (CH$_3$), 26.65 (CH$_2$), 27.79 (CH), 36.90 (CH$_2$), 39.68 (CH$_2$), 50.98 (CH$_2$), 123.92 (CH), 124.28 (CH), 131.32 (C), 135.38 (C), 202.96 (CH=O)

Infrared absorption spectrum (CCl$_4$: cm$^{-1}$): 2963, 2921, 2712, 1726, 1450, 1379, 1106, 833

EI-MS data (27 eV): 222 (M+; 3), 204 (3), 189 (5), 179 (65), 161 (30), 135 (10), 123 (70), 109 (75), 93 (35), 81 (50), 69 (100), 55 (40), 41 (100)

Specific rotation: $[\alpha]_D^{20}$ +4.6 (c 1.0, MeOH)

Example 6

To a 100-ml flask, 0.3 g (GC purity: 91.5%, 0.275 g, 0.99 mmmol) of N,N-diethyl-3,7-11-trimethyldodeca-1,6,10-trien-1-amine (obtained in Example 3), 50 ml of toluene, and 5 ml of 1 N aqueous sulfuric acid were added, and stirred at 15° C. for 10 minutes (conversion: 99% or higher). After the aqueous layer was removed, the organic layer was washed twice with 20 ml of a 10% sodium carbonate solution, and further was washed twice with 20 ml of water.

After completion of the washing, first, toluene was removed by Claisen distillation, and then 0.17 g (GC purity: 99.1%, optical purity: 89.0% e.e., 0.168 g, 0.76 mmol) of (3S)-dihydrofarnesal was obtained at a boiling point of 65 to 70° C./20 Pa in a yield of 77%.

Physical Data of (3S)-Dihydrofarnesal

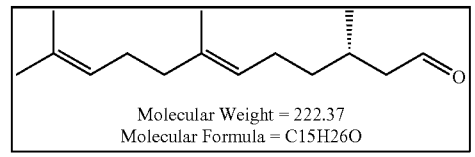

Molecular Weight = 222.37
Molecular Formula = C15H26O

NMR Data $^1$H-NMR (500 MHz, CHLOROFORM-D): δ 0.98 (d, J=6.7 Hz, 3H), δ 1.25-1.4 (m, 2H), δ 1.60 (s, 3H×2), δ 1.68 (s, 3H), δ 1.95-2.1 (m, 7H), δ 2.23 (ddd, J=2.7, 8.0, 16.0 Hz, 1H), δ 2.41 (ddd, J=2.1, 5.6, 16.0 Hz, 1H), δ 5.1 (m, 1H×2), δ 9.76 (t, J=2.7 Hz, 1H)

$^{13}$C-NMR (125 MHz, CHLOROFORM-D): δ 15.97 (CH$_3$), 17.67 (CH$_3$), 19.89 (CH$_3$), 25.28 (CH$_2$), 25.67 (CH$_3$), 26.67 (CH$_2$), 27.80 (CH), 36.91 (CH$_2$), 39.70 (CH$_2$), 50.99 (CH$_2$), 123.92 (CH), 124.29 (CH), 131.34 (C), 135.39 (C), 202.97 (CH=O)

Infrared absorption spectrum (CCl$_4$: cm$^{-1}$): 2963, 2921, 2712, 1726, 1450, 1379, 1106, 833

EI-MS data (27 eV): 222 (M+; 3), 204 (3), 189 (5), 179 (40), 161 (20), 135 (5), 123 (40), 109 (50), 93 (20), 81 (30), 69 (100), 55 (30), 41 (85)

Specific rotation: [α]$_D^{20}$ −3.7 (c 0.5, MeOH)

Synthesis Example 2

To a 20-m; flask, 1.11 g (GC purity: 99.1%, 1.10 g, 4.95 mmol) of (3R)-dihydrofarnesal (obtained in Example 5) and 10 ml of methanol were added, and stirred at 15° C. Subsequently, 0.189 g (5 mmol) of sodiumborohydride (NaBH$_4$) was added thereto, followed by stirring at 15° C. for 30 minutes (conversion: 99% or higher). After completion of the reaction, 10 ml of 1 N hydrochloric acid water and toluene were added, followed by stirring at 15° C. for 10 minutes. Then, the aqueous layer was removed. Subsequently, the organic layer was washed once with 20 ml of a 10% sodium carbonate solution, and further twice with 20 ml of water.

After completion of the washing, first, toluene was removed by Claisen distillation, and then 0.97 g (GC purity: 99.5%, 0.965 g, 4.30 mmol) of (3R)-dihydrofarnesol was obtained at a boiling point of 85 to 90° C./20 Pa in a yield of 87%.

Physical Data of (3R)-Dihydrofarnesol

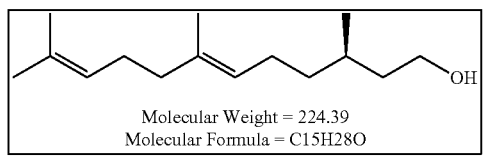 [SMILES: CC(C)=CCC/C(C)=C/CC[C@@H](C)CCO]

Molecular Weight = 224.39
Molecular Formula = C15H28O

NMR Data $^1$H-NMR (500 MHz, CHLOROFORM-D): δ 0.91 (d, J=6.7 Hz, 3H), δ 1.15-1.25 (m, 1H), δ 1.3-1.45 (m, 2H), δ 1.65-1.75 (m, 2H), δ 1.60 (s, 3H×2), δ 1.68 (s, 3H), δ 1.95-2.1 (m, 6H), δ 3.7 (m, 2H), δ 5.1 (m, 2H)

$^{13}$C-NMR (125 MHz, CHLOROFORM-D): δ 15.94 (CH$_3$), 17.65 (CH$_3$), 19.55 (CH$_3$), 25.33 (CH$_2$), 25.66 (CH$_3$), 26.71 (CH$_2$), 29.19 (CH), 37.17 (CH$_2$), 39.72 (CH$_2$), 39.92 (CH$_2$), 61.22 (CH$_2$), 124.36 (CH), 124.58 (CH), 131.26 (C), 134.86 (C)

Infrared absorption spectrum (CCl$_4$: cm$^{-1}$): 3329, 2914, 1451, 1377, 1106, 1057, 1010, 835

EI-MS data (27 eV): 224 (M+; 2), 209 (2), 181 (30), 163 (20), 137 (5), 123 (55), 109 (15), 95 (50), 81 (80), 69 (100), 55 (30), 41 (70)

Specific rotation: [α]$_D^{20}$ +5.0 (c 1.0, CHCl$_3$)
(the compound was determined to be the 3R-isomer on the basis of comparison with the data in Reference Document: Acta. Chem. Scand., 25, 1685-1694 (1971))

The invention claimed is:

1. A method for producing an optically active 2,3-dihydrofarnesal of formula (1):

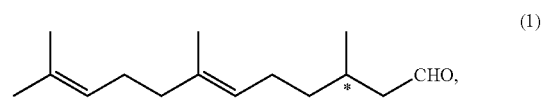 [SMILES: CC(C)=CCC/C(C)=C/CCC(C)CC=O]

(1)

wherein * represents an asymmetric carbon atom, the method comprising:
subjecting β-farnesene of formula (2) to amination in the presence of a lithium salt of an amine:

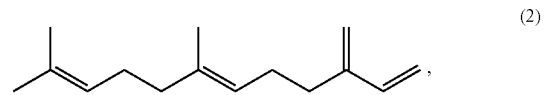

(2)

to obtain (2E)-farnesyl allylamine of general formula (3):

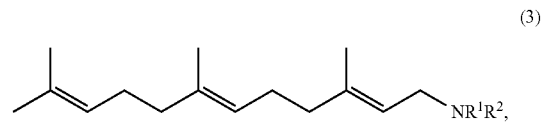

(3)

wherein R$^1$ and R$^2$ are each independently selected from the group consisting of a hydrogen atom, optionally substituted alkyl groups having 1 to 20 carbon atoms, optionally substituted 3-to 8-membered alicyclic groups, optionally substituted aryl groups having 6 to 15 carbon atoms, optionally substituted heterocyclic groups having 2 to 15 carbon atoms, and optionally substituted aralkyl groups having 7 to 12 carbon atoms, provided that R$^1$ and R$^2$ do not represent hydrogen atoms at the same time, or R$^1$ and R$^2$ may be bonded to each other to form a ring;
subsequently subjecting the (2E)-farnesyl allylamine to asymmetric isomerization to obtain an optically active farnesyl enamine of general formula (4):

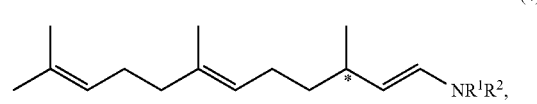

(4)

wherein R$^1$, R$^2$, and * have the same meanings as defined above; and
further subjecting the optically active farnesyl enamine to solvolysis.

2. The production method according to claim 1, wherein the asymmetric isomerization is conducted by using
a rhodium monocationic complex of general formula (5):

[Rh(olefin)L]$^+$X$^-$     (5), wherein the olefin is ethylene, 1,3-butadiene, cyclooctadiene, norbornadiene, or cycloocta-1,5-diene, X is ClO$_4$, BF$_4$, PF$_6$, or PCl$_6$, and L is an optically active bidentate phosphine ligand, or
a rhodium dinuclear complex of general formula (6):

[Rh(L)$_2$]$^+$X$^-$     (6), wherein X and L have the same meanings as defined above.

* * * * *